United States Patent [19]
Chang et al.

[11] Patent Number: 5,631,965
[45] Date of Patent: May 20, 1997

[54] HEARING PROTECTOR

[76] Inventors: Joseph S. Chang, 325 Amess Street, East Brunswick, Victoria, 3057; Yit C. Tong, 1 Charles Street, Kew, Victoria, 3101, both of Australia

[21] Appl. No.: 356,183
[22] PCT Filed: Jun. 18, 1993
[86] PCT No.: PCT/AU93/00295
 § 371 Date: Feb. 15, 1995
 § 102(e) Date: Feb. 15, 1995
[87] PCT Pub. No.: WO94/00089
 PCT Pub. Date: Jun. 6, 1994

[30] Foreign Application Priority Data

Jun. 19, 1992 [AU] Australia ................ PL3021/92

[51] Int. Cl.⁶ .................................................. A61F 11/06
[52] U.S. Cl. .................................. 381/72; 381/74
[58] Field of Search ........................ 381/72, 71, 74, 381/189, 183, 68.6, 94, 68; 181/129–130

[56] References Cited

U.S. PATENT DOCUMENTS 3,952,158 4/1976 Kyle et al. .................. 381/72
5,002,151 3/1991 Oliveira et al. ............ 181/130

*Primary Examiner*—Curtis Kuntz
*Assistant Examiner*—Vivian W. Chang
*Attorney, Agent, or Firm*—Ladas & Parry

[57] ABSTRACT

An active in the ear hearing protector having an ear piece (13) and a casing (12) attachable to the ear piece, the ear piece being positionable in the ear canal of a user so as to peripherally acoustically seal the ear canal and such that the attached casing (12) is positioned externally of the ear canal. The casing (12) incorporates a microphone (14) for receiving external acoustic sound signal and a signal processing circuit (15) for receiving electrical signal from the microphone and correspondingly causing a loudspeaker (16) in the casing to generate sound signal for direction down a tube (34) extending through the ear piece to be transmitted to the ear canal. The electrical circuit (15) is arranged to limit the electrical signal delivered to drive the loudspeaker whereby to limit the sound pressure of sound signal delivered from the loudspeaker to the ear canal via the tube (34).

29 Claims, 6 Drawing Sheets

HEARING PROTECTOR

BACKGROUND OF THE INVENTION

1. Field of the Invention

This invention relates to a hearing protector.

2. Description of the Prior Art

There are situations in military services, industry, sports involving the use of fire arms, aviation and the like, where persons are exposed to loud sounds at sound pressure levels in excess of those which are known to cause permanent hearing damage. To minimize the degree of heating damage incurred in these situations, hearing protectors in the form of earplugs, earmuffs, or a combination of earplugs and earmuffs can be worn. These hearing protectors can be classified as passive or active, and linear or nonlinear.

LINEAR-PASSIVE HEARING PROTECTORS: Linear protectors of the passive type in the form of earplugs or earmuffs are designed to attenuate incoming sound waves of different intensifies by approximately the same number of decibels before they reach the eardrum—that is, the mount of attenuation is independent of the sound pressure level of the incoming sound wave. The disadvantage of these linear hearing protectors of the passive type is that, although the wearer is protected from loud sounds, his/her ability to hear speech sounds and warning signals at sound pressure levels which normally produce low to medium loudness in the absence of the protector is impaired.

NONLINEAR-PASSIVE HEARING PROTECTOR: A nonlinear protector of the passive type may be in the form of an earplug with a small aperture. The attenuation characteristics of this type of earplugs are level-dependent and therefore nonlinear in that only incoming sound waves at levels greater than, say, 110 dB SPL are attenuated. These nonlinear earplugs therefore provide protection against intense impulse noises such as gunfire which produces peak sound pressure levels in excess of 110 dB SPL, but transmit sounds unattenuated at levels below 110 dB SPL. One disadvantage of these nonlinear earplugs of the passive type is that, at levels greater than 110 dB SPL, they provide less attenuation than the linear earplugs. Another disadvantage is that exposure to unattenuated loud sounds at levels greater than 90 dB SPL is known to cause permanent hearing damage. For a discussion of the attenuation characteristics of these nonlinear-passive hearing protectors, see for example E. A. G. Shaw, "Hearing Protector Design Concepts and Performance Limitations", Personal Hearing Protection in Industry, P. W. Alberti Editor, 1982, Raven Press, N.Y.

NONLINEAR-ACTIVE MUFF: U.S. Pat. No. 4,064,362 (Williams); U.S. Pat. No. 3,952,158 (Kyle et al.); and U.S. Pat. No. 3,394,226 (Andrews) describe non-linear protectors of the active type in the form of an muff, being designed to improve communication. A protector of this type contains, inside an earmuff enclosure, a microphone, an electronic circuit, a small loudspeaker and a battery. The microphone converts the incoming sound wave originating exteriorly of the earmuff enclosure to an electrical signal which is processed by the electronic circuit containing a nonlinear compression amplifier and other signal conditioning circuits. For incoming sound waves at sound pressure levels which normally produce low to medium loudness in the absence of the protector, the amplification characteristic of the compression amplifier is approximately linear with a fixed gain. For incoming sound waves at sound pressure levels which normally produce loud hearing sensations, the amplification characteristic of the compression amplifier is nonlinear in that its gain is inversely related to the sound pressure level of the incoming sound wave. The electrical output signal of the electronic circuit is delivered to the loudspeaker which converts the electrical signal back to sound inside the earmuff at the pinna. The electronic components of the electronic circuit arc chosen so that, for incoming sound waves which normally produce low to medium loudness, the sound pressure level at the pinna produced by the loudspeaker is approximately the same as that produced by the incoming sound wave in the absence of the earmuff. On the other hand, for incoming sound waves which normally produce loud hearing sensations, the sound pressure level at the pinna produced by the loudspeaker is less than that produced by the incoming sound wave in the absence of the earmuff as a result of the nonlinear behaviour of the compression amplifier. This protector offers unattenuated communication for speech and warning signals at low to medium sound pressure levels against a quiet background, and provides protection against harmfully loud noises by an mount approximately equal to that provided by a passive muff. The major disadvantages of this active protector include (i) difficulty in maintaining an adequate contact between the head of the wearer and the seals of the earmuff due to interference from ,the temple bars of safety glasses and/or long hair; (ii) poor condition of the seals; (iii) poor headband tension, (iv) bulkiness when used in conjunction with other safety devices such as welding shields, hard hats, helmets, respirators, or a combination of these safety devices; (v) discomfort due to the weight of the earmuff and the irritation in an environment of high ambient temperature or high humidity. Note that these disadvantages also apply to passive earmuffs.

NONLINEAR-ACTIVE CUSTOM MOULDED PLUG: Another nonlinear active protector uses the same electronic principles as the nonlinear active muff, but is in the form of a custom moulded in-the-car hearing aid with miniature hearing aid components housed in a custom-made earmould for fight fitting into the outer ear of the wearer. The miniature components include a microphone, a small loudspeaker (also known as a receiver), an electronic circuit and a battery. As in the ease of the nonlinear active earmuff, this in-the-ear protector offers unattenuated communication for speech and warning signals at low to medium sound pressure levels against a quiet background, and provides protection against harmfully loud noises. The major disadvantages of this device include: (i) difficulty in achieving a fight fit between the earmould and outer ear using existing moulding techniques for adequate sound attenuation; (ii) difficulty in maintaining the original fit due to wear, tear and shrinkage of the custom-made earmould; (iii) increased costs because the custom-made moulds must be fired by experienced technicians; (iv) clogging of the sound transmission path in the earmould by ear wax and difficulty in removing the ear wax because only the ear canal end of the sound mission path is accessible to the user;, (v) increased maintenance costs because the units must be sent back to the manufacturer or dealer for proper maintenance to remove ear wax and to repair damage caused by users who tried to clean out the wax; and (vi) lack of transferability from user to user because of the custom-made earmould. These disadvantages are commonly encountered generally in the use of in-the-ear hearing aids.

Other Related Art

U.S. Pat. No. 5,002,151 (Oliveira et al.) discloses a disposable compressible polymeric foam sleeve to be disposably attached to a hearing aid. In the Oliveira et al.

patent, the foam sleeve "can be compressed to be fully insertable into a person's ear and allowed to recover to become wedged in the ear canal", and it is preferably attached to the hearing aid by mating of screw threads. However, the foam sleeve in the Oliveira et al. patent is not intended for use in heating protectors and does not include adequate acoustic seals which are required in hearing protectors to reduce substantially the direct transmission of incoming sound waves off,hating exteriorly of the outer ear to the eardrum.

SUMMARY OF THE INVENTION

In accordance with the present invention, there is provided a hearing protector comprising a sound processor for receiving at an input thereof exterior sound and generating therefrom at an output thereof corresponding processed sound limited to intensifies not substantially exceeding a predetermined sound pressure level, and an ear piece detachably mounted to said sound processor and having sound channeling means for passage of said processed sound away from said sound processor, said hearing protector being insertable into the outer ear so as to position said sound processor for receiving at said input said exterior sound, being sound originating exteriorly of the outer ear, and for directing said processed sound, as generated from said exterior sound by said sound processor, to the eardrum via said sound channelling means of said ear piece, while substantially precluding direct transmission of said exterior sound to the eardrum.

The invention also provides an active in-the-ear hearing protector made suitable to be sealingly inserted, one in each ear canal of a wearer, for protecting the wearer from loud sounds while enabling the wearer to hear sounds at nonharmful sound pressure levels, comprising:

(a) a casing having distal and proximal ends and an exterior surface between said distal and proximal ends and having in its interior:
(i) microphone means for converting exterior sounds originating exteriorly of the outer car to an electrical microphone signal,
(ii) electronic means for converting said electrical microphone signal to an electrical output signal, said electronic means including electronic compression means for controlling the amplitude of said electrical output signal to be proportional to the amplitude of said electrical microphone signal when the amplitude of said electrical microphone signal is below a pre-determined threshold value, and for automatically limiting the amplitude of said electrical output signal to within a pre-determined narrow dynamic range when the amplitude of said electrical microphone signal increases beyond said pre-determined threshold value so that the amplitude of said electrical output signal is not allowed to exceed a predetermined maximum amplitude,
(iii) sound reproducer means for producing sound waves in response to said electrical output signal,
(iv) sound transmitting means sealingly attached to the acoustic outlet of said sound reproducer means and to the wall of said distal end of said casing for delivering sound waves produced by said sound reproducer means to the exterior of said distal end of said casing, whereby transmission of said exterior sounds through said easing and then said sound transmitting means is minimised,
(v) battery means for supplying power for operation of said active hearing protector, (b) an on/off switching means which is partly located exteriorly to and proximally of said casing, whereby the electrical power supplied by said battery can be switched on or off exteriorly to said easing at the proximal end of said easing, (c) a user detachable ear piece comprising:
(i) a sound transmitting tube,
(ii) a polymeric retarded recovery foam member having distal and proximal ends, said foam member sealingly surrounding said sound transmitting tube, whereby an acoustic seal is formed between said sound transmitting robe and said foam member especially when said foam member is mechanically compressed to miniraise transmission of said exterior sounds to the eardrum, said foam member defining a substantially cylindrical clement having a slow compression recovery rate, whereby said ear piece may be mechanically compressed and inserted distal end first into an ear canal of the wearer and will thereupon expand to form an elongated acoustic seal therein between the ear piece and a substantial surface area of the ear canal to miniraise transmission of said exterior sounds to the eardrum,
(iii) connector means attached to said proximal end of said polymeric foam member for detachably and sealingly attaching said detachable car piece to the distal portion of said easing and for sealingly connecting said sound transmitting means attached to said sound reproducer means to said sound transmitting tube in said detachable ear piece, whereby sounds produced by said sound reproducer means are transmitted through an acoustically sealed sound transmission path comprising said sound transmitting means in said casing and said sound transmitting tube in said car piece to the ear canal and eardrum so that the transmission of said exterior sounds through said connector means to the eardrum is minimized.

BRIEF DESCRIPTION OF THE DRAWINGS

The invention is further described by way of example only with reference to the accompanying drawings, in which.

DETAILED DESCRIPTION OF THE PREFERRED EMBODIMENTS

Figure 1:
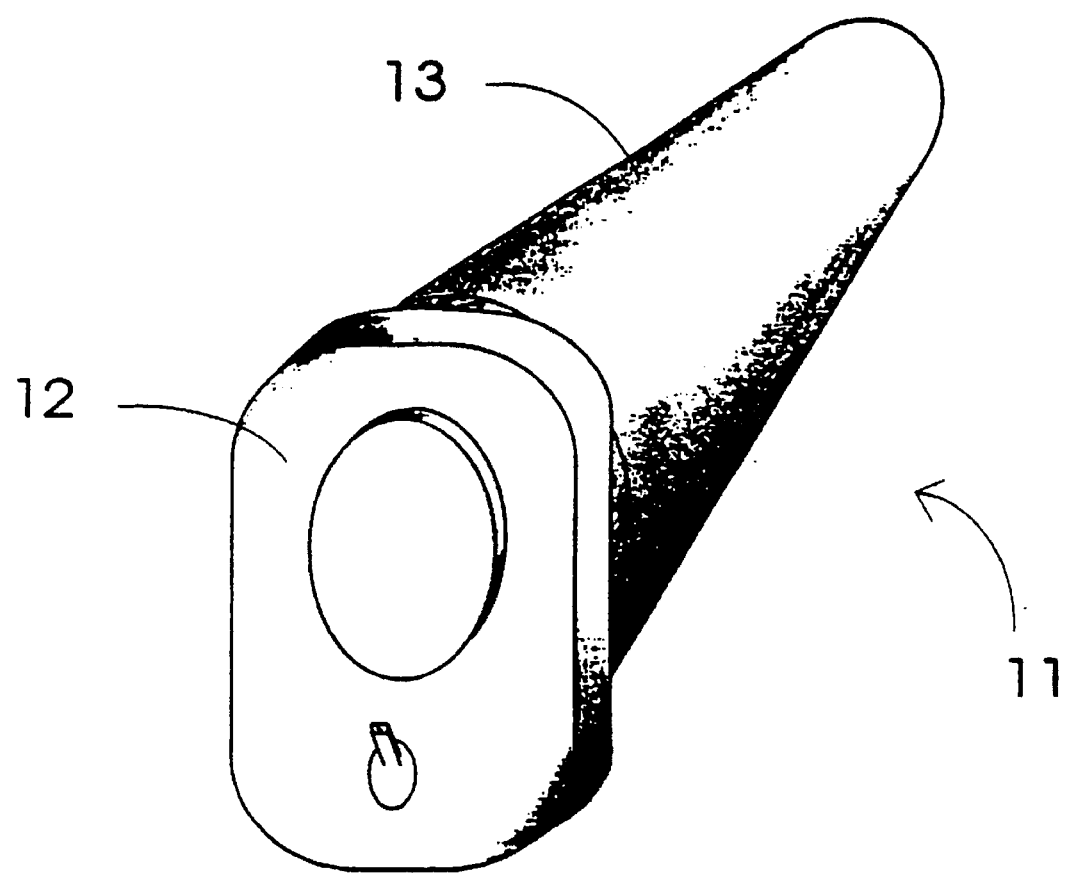
FIG. 1 is a diagrammatic view of the hearing protector embodying the present invention.
Figure 2:
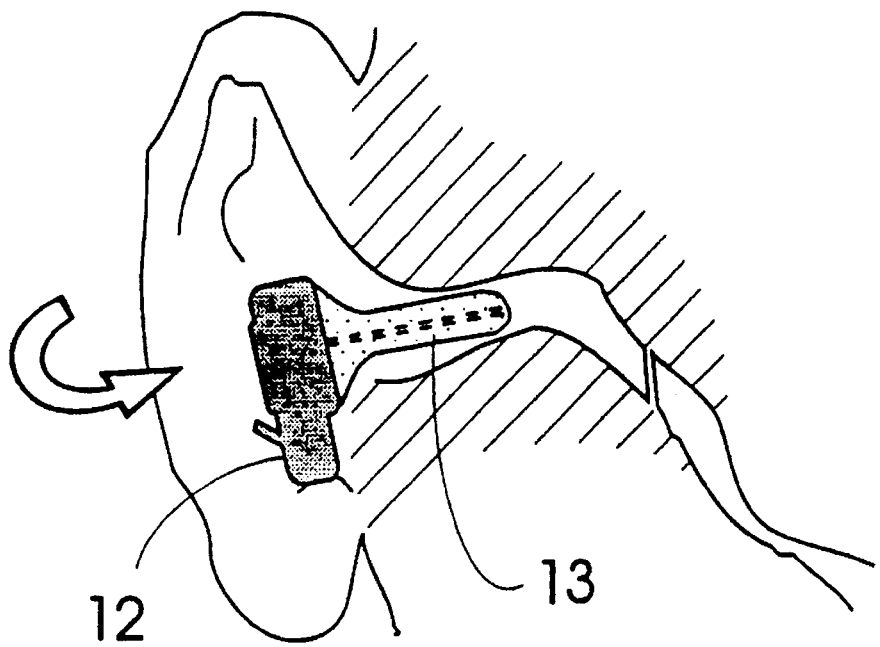
FIG. 2 is a diagrammatic view illustrating the insertion of the hearing protector of FIG. 1 embodying the invention into the car canal with the detachable car piece of the protector in its mechanically compressed state.
Figure 3:
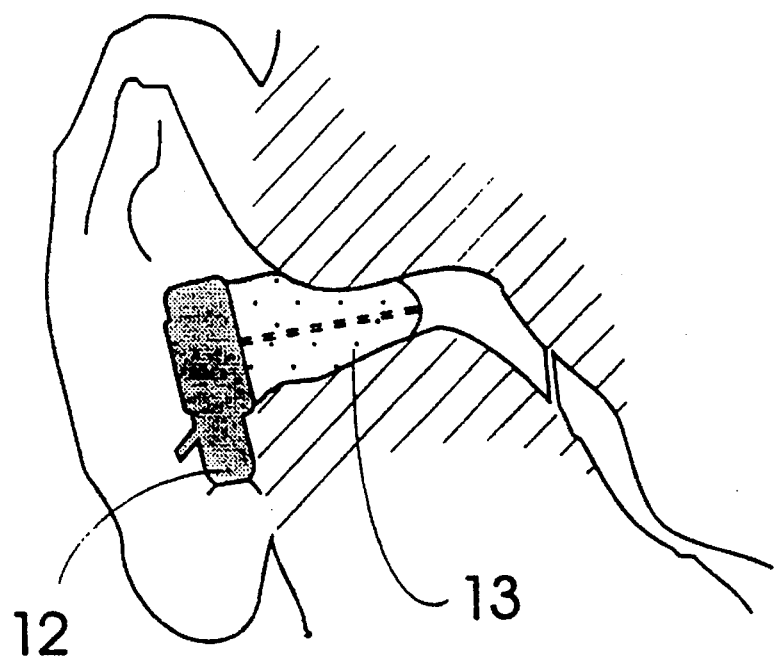
FIG. 3 is a diagrammatic view illustrating the hearing protector of FIG. 1 after its detachable ear piece has expanded to engage the circumference of a portion of the car canal of a wearer.

The hearing protector 11 shown in FIG. 1 comprises a casing 12 and an attached ear piece 13. Thus, the casing 12 extends from a proximal end to a distal end at which it is connected to a proximal end of the ear piece 13. The ear piece is formed of an earplug member made of a retarded recovery foam which can be compressed, as shown in FIG. 2, to permit the ear piece to be inserted distal end first into the ear canal of a user, such that when the earplug member recovers by subsequently expanding, it seals against the surface of the ear canal as shown in FIG. 3. In this condition, the casing 12 is outermost and the hearing protector 11 is ready for use.

Figure 4:
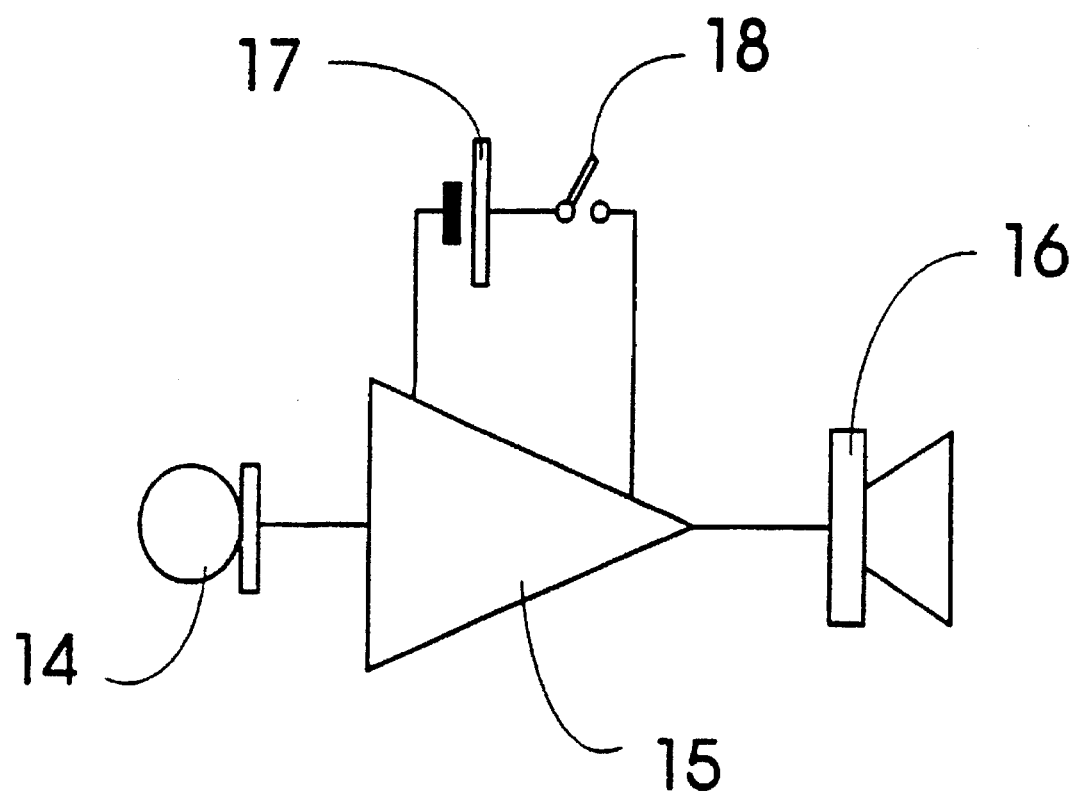
FIG. 4 illustrates a most general block diagram of the electronics of a nonlinear active hearing protector.

The casing 12 incorporates an active sound processor formed from electronic/electroacoustic components as shown in FIG. 4. These include a microphone 14, an electronic circuit 15, a small loudspeaker 16, a battery 17 and an on/off switch 18. Microphone 14 converts the incoming sound wave originating exteriorly of the outer ear to an electrical signal which is processed by electronic circuit 15 which contain a nonlinear compression amplifier and other signal conditioning circuits. For incoming sound waves at sound pressure levels which normally produce low to medium loudness in the absence of the protector, the amplification characteristic of the compression amplifier is approximately linear, with a fixed gain. For incoming sound waves at sound pressure levels which normally produce loud hearing sensations, the amplification characteristic of the compression amplifier is nonlinear in that its gain is inversely related to the sound pressure level of the incoming sound wave.

The electrical output signal of electronic circuit 15 is delivered to loudspeaker 16 which converts the electrical signal back to sound inside the hearing protector 11 in the ear canal. The electronic components of the electronic circuit 15 are chosen so that, for incoming sound waves which normally produce low to medium loudness, the sound pressure level in the ear canal produced by loudspeaker 16 is approximately the same as that produced by the incoming sound wave in the absence of the protector. On the other hand, for incoming sound waves which normally produce loud hearing sensations, the sound pressure level in the ear canal produced by loudspeaker 16 is less than that produced by the incoming sound wave in the absence of the protector, and is not allowed to exceed a maximum level, to protect the wearer from harmful noise exposure. Battery 17 provides the power source for hearing protector 11, which may be turned on or off by operating switch 18.

Figure 5:
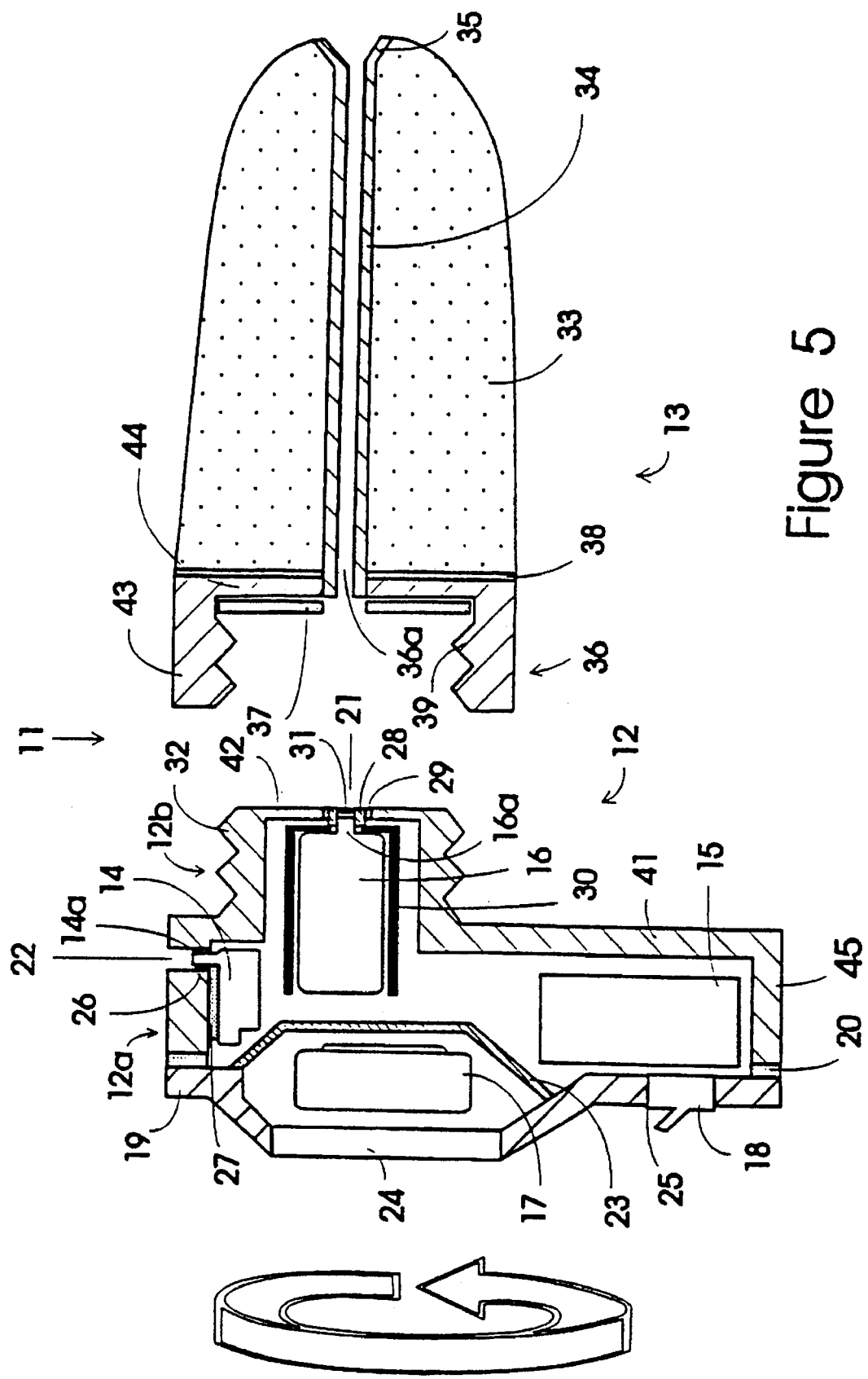
FIG. 5 is a schematic section through an in-the-ear hearing protector designed in accordance with the present invention.

Referring now to FIG. 5, the casing 12 has an proximal section 12a, a distal section 12b and a face plate 19. Section 12a is formed with a longitudinal wall 45 which is somewhat cylindrical, the face plate 19 at its proximal end, and a transverse wall 41 at its distal end. Transverse wall 41 has a hole, which is offset from the geometric centre of the wall.

Face plate 19 is secured to section 12a of casing 12 by a suitable solvent 20. Sections 12a and 12b are moulded as one plastic piece.

Battery 17 is located inside the casing 12, in a battery holder 23 closed by a removable battery cover 24. Holder 23 and cover 24 are integral parts of face plate 19. Electronic circuit 15 of the hearing protector is mounted in the easing 12 on face plate 19, and is connected to switch 18, which is also mounted internally on face plate 19, but such that its actuating arm extends exteriorly through an opening 25 in face plate 19. The sound inlet 14a of a miniature heating aid microphone 14 is tightly inserted into an orifice 22 through the longitudinal wall 45 of section 12a and is further secured by applying solvent 26 on the wall of sound inlet 14a before the insertion. The body of microphone 14 is secured on the interior surface of section 12a by using paste 27.

Cylindrical casing section 12b projects outwardly from transverse wall 41 of casing section 12a, located opposite face plate 19. This defines an internal cavity which communicates with the interior of section 12a through the hole in transverse wall 41 but which is substantially closed by an end wall 42 of section 12b. Casing section 12b has a circular orifice 21 through the end wall 42. A short piece of flexible plastic tube 28 with an inner diameter mailer than the outside diameter of the sound outlet 16a of loudspeaker 16 and outside diameter greater than the diameter of circular orifice 21 is tightly inserted into orifice 21 so as to project a short distance into the cavity in distal section 12b, and is further secured by applying solvent 29 on the wall of robe 28 before the insertion. A miniature hearing aid loudspeaker 16 is fitted into a rubber boot 30 to reduce the effects of shock and vibration and these are both positioned in the internal cavity in sections 12a and 12b. The sound outlet 16a of loudspeaker 16 is tightly inserted into the end of flexible plastic robe 28 which is inside section 12b. A hearing aid acoustic damper 31 which modifies the frequency response characteristics of hearing protector 11 to approximate the response characteristics for normal hearing is inserted into flexible plastic tube 28 from the outside of casing 12.

The external surface of section 12b of casing 12 is formed with a male screw thread 32.

The ear piece 13 consists of an earplug member 33 made of polymeric retarded recovery foam, which surrounds a flexible robe 34 with a flared end 35. The ear piece also has a moulded plastic connector 36. Connector 36 is substantially cup shaped, having a peripheral wall 43 and transverse wall 44. Wall 44 has a centre hole 36a whose diameter is the same as the outside diameter of flexible tube 34. A resilient washer 37 is positioned in connector 36, within wall 43 on the inner side of wall 44. Washer 37 has a centre hole whose diameter is the same as the outside diameter of flexible tube 34. Wall 44 of connector 36 is bonded to earplug member 33 at one end of the earplug member remote from the flared end of the robe 34 by using solvent 38.

Wall 43 of connector 36 has an internal female screw thread 39, which mates with male screw thread 32 of section 12b of casing 12 to join the connector and ear pie together. The washer 37 is then compressed between wall 42 of section 12b of casing 12 and the wall 44 of connector 36, so as to provide a good acoustic seal between the easing 12 and car piece 13. It will be realised that the resilient washer 37 in connector 36 may be omitted, if a good enough acoustic seal between casing 12 and ear piece 13 can be established without the use of a washer.

Flexible robe 34 is snugly fitted into centre hole 36a of connector 36 but does not protrude beyond centre hole 36a so that when ear piece 13 is threaded onto casing 12, a continuous and uninterrupted passage is formed between the acoustic damper 31 and the opening of car piece 13 at flared end 35.

The construction of flared end 35 ensures that flexible tube 34 is not blocked by the ear plug member 33 and sound waves produced by loudspeaker 16 can reach the car canal and then the eardrum via the tube 34.

The flexible tube 34 is not restricted to having the flared end 35 shown in FIG. 5. A flexible robe without a flared end may be used, such as one which extends for a short distance into the ear canal beyond the distal end of the ear plug member to avoid blockage of the robe by the ear plug member.

Face plate 19 and its associated battery holder 23 and battery cover 24, electronic circuit 15, microphone 14, loudspeaker 16, rubber boot 30, acoustic damper 31 and on/off switch 18 may be formed of components customarily used in standard in-the-ear hearing aids. Flexible plastic tube 28 is most preferably a clear, flexible PVC tubing such as those used in standard hearing aid construction. Paste 27 is preferably silicone rubber such as Silastic® Marine Sealant manufactured by Dow Coming. Solvents 20, 26, 29 and 38 are preferably cyanoacrylate instant adhesives such as Supa Glue manufactured by Selleys Chemical Company. Preferred materials from which casing 12 and connector 36 may be moulded include Acrylonitrile-Butadiene-Styrenc (ABS) and High and Low Density Polyethylene. Preferred materials for resilient washer 37 include natural and synthetic rubber, cork, felt, and sponge rubber, see for example C. E. Credo, "Vibration Isolation", Handbook of Noise Control, C. M. Harris Editor, 1957, McGraw-Hill Book Company, N.Y. Ear plug member 33 is most suitably formed from a foam plastic that has retarded recovery. Use of this material allows earplug member 33 to be mechanically compressed substantially but to re-expand into sealing engagement with the ear canal of a wearer within about 1–40 seconds. The exterior surface of earplug member 33 preferably is substantially cylindrical, tapering slightly inwardly towards its end which is inner most in the ear canal, to facilitate insertion into a wearers ear canal. Earplug member 33 may be formed by moulding, and its exterior surface may possess a somewhat smooth skin which is devoid of large cells that could pick up dirt and is therefore largely imperious to soil and liquid contamination. One such foam earplug is described in U.S. Pat. No. 4,774,938 (Leight). The earplug member of the heating protector according to this invention is not restricted to being the form of tapered earplug member 33 shown in FIG. 5, but may for example be completely To receive flexible tube 34, earplug member 33 may be initially coaxially bored throughout its length with a central corer. Flexible robe 34 can be then inserted into the coaxial bore of earplug member 33. Alternatively, earplug member 33 may be moulded onto flexible tube 34 during the moulding process for the manufacture of the earplug member. In either method, a fight fitting is formed between flexible robe 34 and earplug member 33.

Preferably, flexible tube 34 is made of soft plastic material such as Silastie® Medical Grade Tubing manufactured by Dow Coming; the internal diameter of this tube preferably is large enough for good sound transmission while its external diameter preferably is small enough to allow the fully compressed earplug member 33 to be easily insertable into a human ear canal.

In operation, ear piece 13 is threaded onto casing 12 as described. Earplug member 33 is mechanically compressed and carefully inserted into the ear canal by the wearer as illustrated in FIG. 2. Earplug member 33 is allowed to expand and form a sealing engagement with the ear canal as illustrated in FIG. 3. The protector 11 is then switched on by means of on/off switch 18.

The tight fitting between loudspeaker 16 and flexible plastic tube 28, and between flexible plastic tube 28 and orifice 21, provide acoustic seals which reduce substantially the intensity of the incoming sound wave originating exteriorly of the outer ear, which may reach the acoustic damper end of flexible plastic tube 28 via the openings in face plate 19, and may then reach the eardrum. As mentioned, when ear pie 13 is threaded onto section 12b of casing 12, resilient washer 37 is mechanically compressed to provide an acoustic seal which reduces substantially the intensity of the incoming sound wave originating exteriorly of the outer ear, which may reach the washer end of flexible tube 34 via screw threads 32 and 39, and may then reach the eardrum. The tight firing between flexible tube 34 and earplug member 33 provides an acoustic seal which reduces substantially the intensity of the incoming sound wave originating exteriorly of the outer ear, which may reach the ear canal and then the eardrum via the coaxial bore of earplug member 33. These acoustic seals assist in reducing the direct transmission of incoming sound waves originating exteriorly of the outer ear to the eardrum to provide protection against harmfully loud noises by an mount approximately equal to that provided by a passive foam earplug.

It will be realised that earplug member 33 is not restricted to being formed from foam plastics, but may use other materials such as vinyls, cured silicones, and other elastomeric formations. When earplug member 33 is formed from these alternative materials other than foam plastics, it will be realised that flexible tube 34 may not be needed and may be replaced by an acoustic passage formed as a coaxial bore of the earplug member during the moulding proems for the manufacture of the earplug member.

It will also be realised that ear piece 13 is not restricted to being attached to casing 12 by mating of screw threads on casing 12 and connector 36, but may be attached to casing 12 by other means such as a coupler with an O-ring.

EXAMPLE

Eight prototype in-the-ear hearing protectors of the present invention as illustrated in FIGS. 1 to 5 were constructed using standard in-the-ear hearing aid components. Each prototype used a Knowles Electronics EM3056 microphone, a Knowles Electronics EH3054 receiver (small loudspeaker), a Genum LD511 compression amplifier, a Knowles Electronics BF3039 acoustic damper, and a Microtronic SW521 on/off switch. In addition, a 312 type zinc air battery, a face plate with dimensions suitable for receiving the 312 battery, and a rubber boot with dimensions suitable for receiving the EH3054 receiver were used. A clear PVC tube with an outside diameter of 2 mm and an internal diameter of 1.4 mm was used as flexible plastic tube 28 in FIG. 5. Silastic® Medical Grade Tubing 602-175 manufactured by Dow Corning with an outside diameter of 1.65 mm and an internal diameter of 0.76 mm was used as flexible tube 34. The casing and connector were constructed on a lathe using clear acrylic material. The face plate 19 was 2 mm in thickness, with overall dimensions of 18 mm×12 mm. The wall of the casing was 1 mm in thickness and had overall outside dimensions of 18 mm×12 mm×5 mm for section 12a; the outside diameter of the section 12b was 9 mm and its overall height is 3 mm. The cylindrical wall of the cylindrical connector was 1.5 mm in thickness, and has an internal diameter of 9 mm. The bottom surface at the earplug member end of the connector had a thickness of 0.5 mm. The overall height of the connector was 3.5 mm. The screw threads were formed using 9 mm tap and die with 0.75 mm pitch. The resilient washer was formed by punching cylinders out of a 0.8 mm thick sheet of rubber. Supa Glue manufactured by Selleys and Silastie® Maxine Sealant manufactured by Dow Corning were used. The earplug member was formed using a Bilsom Form foam earplug manufactured by Bilsom. The foam earplug, approximately 23 mm in length, was initially coaxially bored throughout its length with a central corer. The Silastic® flexible tube was then inserted into the coaxial bore of the earplug member. The Silastic® flexible tube extended approximately 0.6 mm beyond the distal end of the earplug member to avoid blocking of the sound transmission path by the foam material.

Testing was conducted on a Knowles Electronics Manikin for Acoustic Research with artificial pinnas, artificial ear canals and artificial eardrums. Test signals were one-third octave bandpass noise at centre frequencies of 125 Hz to 8 kHz, and impulse noise generated by a toy pistol with cap at a distance of 5 cm from the left artificial pinna. All sound pressure levels were measured A-weighted. For bandpass noise measurements, a measuring time constant corresponding to "RMS FAST" was used; for impulse noise measurements, peak sound pressure levels were recorded. The sound pressure level at the left artificial pinna is designated $P_{pinna}$, and was monitored using a half-inch condenser microphone.

Four sound pressure level measurements were made at the left artificial eardrum: (1) $P_{open}$ for an unobstructed left artificial ear canal; (2) $P_{foam}$ for a Bilsom Form foam earplug alone in left artificial ear canal; (3) $P_{plugoff}$ for an active earplug of the present invention with its electrical power switched off in the left artificial ear canal; and (4) $P_{plugon}$ for an active earplug of the present invention with its electrical power switched on in the left artificial ear canal. Both Bilsom foam and active earplug of the present invention were initially compressed and inserted into the artificial ear canal, and were then allowed to expand and form an acoustic seal with the canal.

Figure 6:
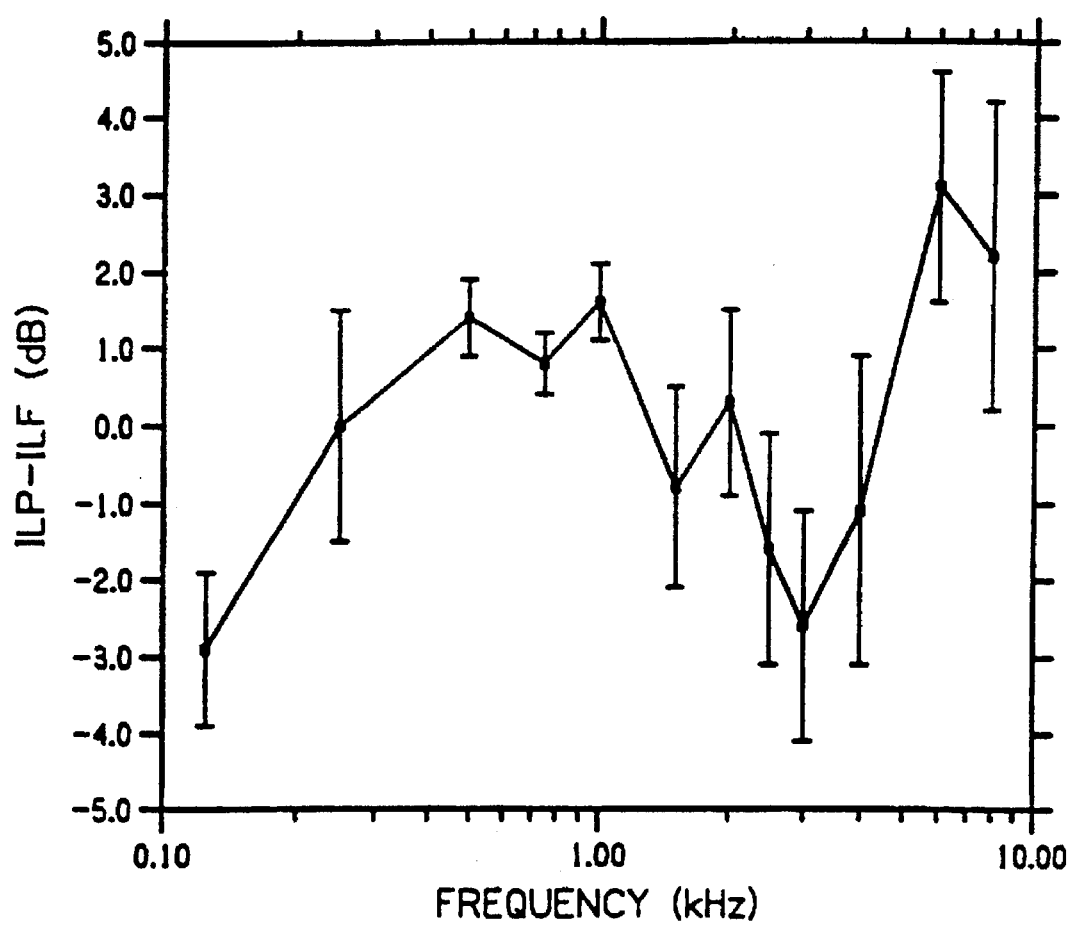
FIG. 6 is a graph presenting the difference in insertion loss measured on a manikin between a conventional foam earplug and the hearing protector of the present invention with its electrical power switched off.

The difference in insertion loss between the Bilsom foam alone and the active earplug of the present invention with its electrical power switched off is shown in FIG. 6 as a function of the centre frequency of the one-third octave bandpass noise. All insertion loss measurements were made with $P_{pinna}$ fixed at a level of 100 dBA. Insertion loss for the Bilsom foam alone is designated ILF, and is deemed as ILF (dBA)=$P_{open}$(dBA)–$P_{foam}$(dBA). Insertion loss for the active earplug with its power switched off is designated ILP, and is defined as ILP (dBA)=$P_{open}$(dBA)–$P_{plugoff}$(dBA). ILF was measured for eight Bilsom foams; the eight foams correspond respectively to the eight prototype active earplug. After the ILF measurements (and the impulse noise measurements to be described later) on the eight foams were completed, the detachable ear pieces of the corresponding eight prototypes were constructed by inserting a Silastic® tube into each foam after the foam had been coaxially bored, and by securing the connector on the proximal end of the foam using Supa Glue as described earlier. ILP measurements were then conducted.

In FIG. 6, each data point and the error bar associated with it represent the mean and standard deviation of the eight values of (ILP–ILF) for the eight prototypes, respectively. From FIG. 6, it can be seen that the difference in insertion loss measured on the manikin between the Bilsom Form foam earplug and the prototype earplug of the present invention with its electrical power switched off is small—that is, the prototype earplug with its power switched off provides approximately the same mount of attenuation and therefore protection as the Bilsom Form foam earplug, indicating that the acoustic seals implemented in the prototype earplugs were effective.

Figure 7:
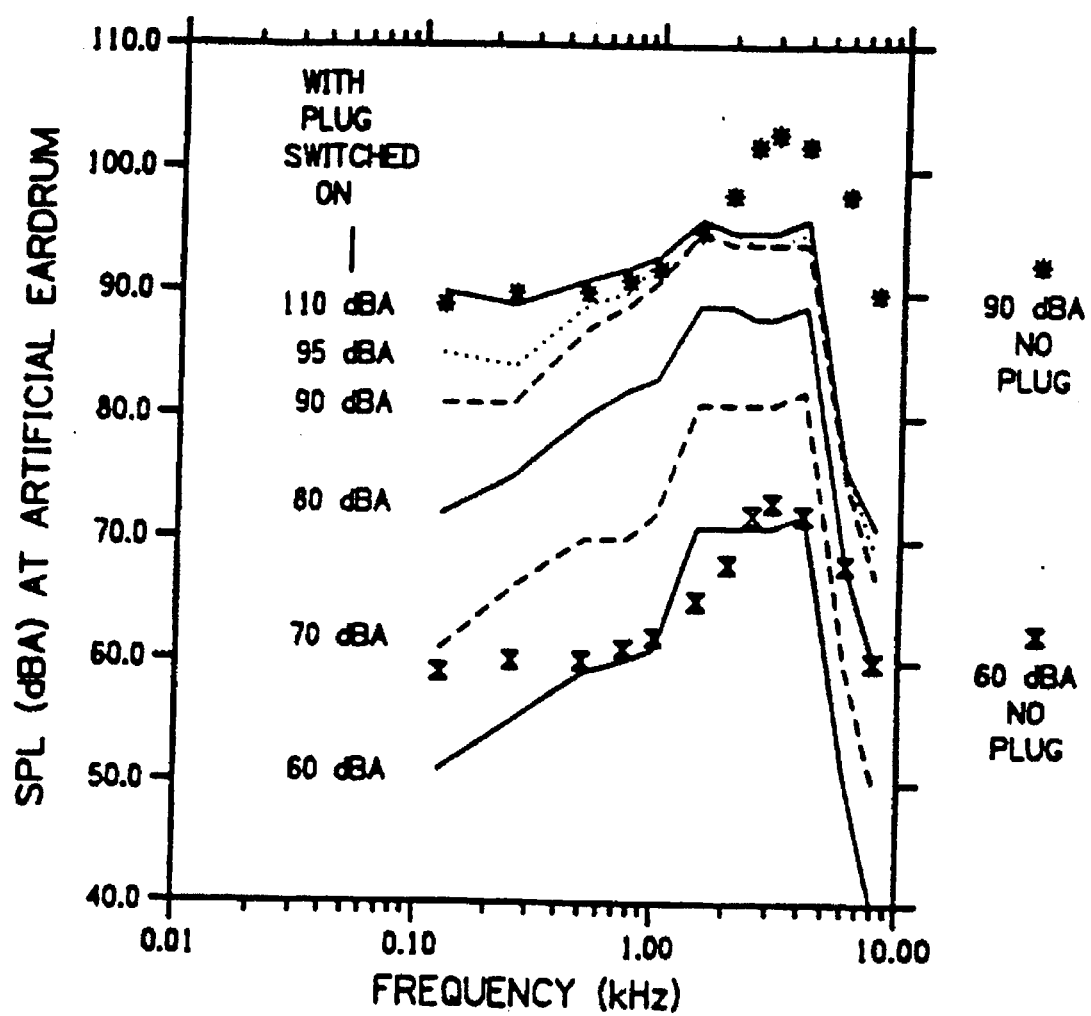
FIG. 7 is a graph presenting the sound pressure levels produced by the small loudspeaker of the hearing protector of the present invention at the artificial eardrum of a manikin for a number of values of sound pressure level at the artificial pinna.

FIG. 7 shows the variations of $P_{plugon}$ for one of the prototype earplugs versus the centre frequency of the one-third octave bandpass noise for a number of levels of $P_{pinna}$.

The variations of $P_{open}$ over frequency for $P_{pinna}$ at 60 dBA and 90 dBA are also shown for comparison. The electronic components of the prototypes were sealed so that, for $P_{pinna}$ below 80 dBA, $P_{plugon}$ produced by the receiver in the prototype is approximately the same as $P_{open}$; on the other hand, for $P_{pinna}$ above 80 dBA, $P_{plugon}$ does not increase linearly with respect to $P_{pinna}$ and is prevented from increasing to levels beyond $P_{open}$ recorded for $P_{pinna}$ at 90 dBA. From FIG. 7, it can be seen that the levels of $P_{plugon}$ for a fixed $P_{pinna}$ of 60 dBA approximate those of $P_{open}$ for the same level of $P_{pinna}$ from 250 Hz to 4 kHz, the major frequency band for speech and common everyday sounds. For levels of $P_{pinna}$ between 60 and 80 dBA, $P_{plugon}$ increases approximately linearly for all the frequencies tested. $P_{plugon}$ is, however, strongly limited for levels of $P_{pinna}$ above 80 dBA, and does not exceed $P_{open}$ recorded for $P_{pinna}$ at the level of 90 dBA. These characteristics shown in FIG. 7 were also observed for the other seven prototypes. The experimental results therefore showed that the active earplug of the present invention offers unattenuated communication for speech and warning signals at low to medium sound pressure levels, and provides protection against harmfully loud noises. $P_{open}$, $P_{foam}$, $P_{plugon}$, and $P_{plugoff}$ were measured for two of the prototypes at the left artificial eardrum when a toy pistol with cap was fired 5 cm from the left artificial pinna. Note that, as mentioned earlier, $P_{foam}$ was measured for each prototype before the construction of the detachable ear piece. The results of these peak sound pressure level measurements are similar for the two prototypes and their results arc pooled and shown in TABLE I. Each entry in the Table represents the mean of ten peak sound pressure measurements. From TABLE I, it can be seen that for a loud impulse noise such as a pistol shot the levels of $P_{foam}$, $P_{plugon}$ and $P_{plugoff}$ are approximately the same. The prototype active earplug of the present invention is therefore effective in protecting the wearer from loud impulse noises.

TABLE 1

| $P_{open}$ | $P_{foam}$ | $P_{plugoff}$ | $P_{plugon}$ |
|---|---|---|---|
| 166 dBA | 105 dBA | 103 dBA | 106 dBA |

The described form of the invention comprises:

(1) a small casing having on its wall an on/off switch and in its interior a microphone, an electronic circuit, a battery, a small loudspeaker (also known as a receiver), and a flexible plastic tube tightly fitted at one end to the acoustic outlet of the loudspeaker and at the other end to an orifice on the wall of the casing, and (2) a detachable ear piece comprising an earplug member made of polymeric retarded recovery foam material, a flexible sound transmission tube sealingly secured inside the earplug member, and a connector which is permanently attached to one end of the earplug member.

Preferably, the detachable ear piece is attached to the casing by mating of screw threads on the connector and the casing. An acoustically sealed sound mission path is formed from the outlet of the small loudspeaker in the casing to the sound transmission tube in the ear piece by the inclusion of a resilient washer which is mechanically compressed between the casing and the connector by the mating of the screw threads.

In operation, the detachable ear piece is connected to the casing by means of the connector on the ear piece. The earplug member made of foam material is mechanically compressed and carefully inserted into the ear canal. The earplug member is allowed to expand and form an acoustically sealing engagement with the ear canal. The active hearing protector is switched on by means of the on/off switch. The microphone converts the incoming sound wave originating exteriorly of the outer ear to an electrical signal which is processed by the electronic circuit containing a nonlinear compression amplifier and other signal conditioning circuits. The electrical output signal of the electronic circuit is delivered to the small loudspeaker which converts the electrical signal back to sound. The sound wave produced by the loudspeaker propagates through an acoustically sealed sound transmission path comprising successively the flexible plastic tube attached to the outlet of the loudspeaker in the casing, the resilient washer, the connector, and the sound transmission tube inside the earplug member of the detachable ear piece, to reach the ear canal and the eardrum. The electronic components of the electronic circuit are chosen so that, for incoming sound waves which normally produce low to medium loudness, the sound pressure level in the ear canal produced by the loudspeaker is approximately the same as that produced by the incoming sound wave in the absence of the protector. On the other hand, for incoming sound waves which normally produce loud hearing sensations, the sound pressure level in the ear canal produced by the loudspeaker is less than that produced by the incoming sound wave in the absence of the protector, and is not allowed to exceed a maximum level to protect the wearer from harmful noise exposure.

The described hearing protector reduces substantially the direct transmission of incoming sound waves originating exteriorly of the outer ear to the eardrum by the acoustic seals provided by:

(1) the tight flags between the flexible plastic tube and the acoustic outlet of the small loudspeaker in the casing, and between the tube and the wall of the casing, (2) the novel design of the connector including the resilient washer on the detachable car piece, (3) the tight fitting between the flexible sound transmission robe and the earplug member of the detachable car piece, and (4) the tight fitting between the earplug member and the car canal.

The sound intensity at the eardrum produced by the incoming sound wave originating exteriorly of the outer car after propagating through these acoustic seals is therefore very much attenuated. The hearing protector of the present invention offers unattenuated communication for speech and warning signals at low to medium sound pressure levels against a quiet background, and provides protection against harmfully loud noises by an amount approximately equal to that provided by a passive foam earplug.

The size of the novel heating protector of the present invention is small and can be fined into the outer car of the wearer in the same manner as an in-the-car hearing aid or nonlinear-active hearing protectors in the form of in-the-car hearing aids. The electroacoustic and electronic components of the hearing protector of the present invention arc those used in conventional in-the-car hearing aids.

The hearing protector described with reference to the drawings offers a number of advantages over conventional nonlinear-active hearing protectors in the form of in-the-car hearing aids using custom-made earmoulds. The earplug member made of foam material of the detachable car piece of the present invention guarantees that the hearing protector is always snugly fitted into the car canal, and the presence of the connector and the casing provides a convenient mechanical means for inserting and extracting the hearing protector from the outer ear. The hearing protector of the present invention can be conveniently acquired off-the-shelf without specialised fitting by trained technicians as required by heating protectors using custom-made earmoulds. Clogging of the sound transmission tube in the detachable ear piece of the heating protector of the present invention by ear wax can be easily cleaned because the detachable ear piece can be easily detached from the casing so that both ends of the sound transmission robe are accessible to the user, and the ear wax can be easily extracted from within the tube by the use of a simple tool such as a fine metallic wire. The detachable ear piece of the hearing protector of the present invention is easy to manufacture and is inexpensive to the user; it can be readily replaced if its earplug member becomes soiled or dirty or if its sound transmission tube is irreparably clogged by ear wax. The casing containing the electronic and electroacoustic components is transferable from user to user.

The hearing protector described with reference to the drawing is a nonlinear active in-the-car hearing protector which reduces substantially the direct Transmission of incoming sound waves originating exteriorly of the outer ear to the eardrum by using acoustic seals.

The hearing protector described with reference to the drawings provides a nonlinear active in-the-ear hearing protector which converts incoming sound waves originating exteriorly of the outer ear to an electrical signal by means of a microphone, processes the electrical signals by means of an electronic circuit, converts the processed electrical signals back to sound waves by means of a small loudspeaker, and delivers the processed sound waves which are now at non-harmful sound pressure levels to the car canal and then the ear drum.

The hearing protector described with reference to the drawings provides a nonlinear active in-the-ear hearing protector with a detachable ear piece which provides a fight fitting between a earplug member on the ear piece and the ear canal, and is easy to insert into and extract from the outer ear.

The hearing protector described with reference to the drawing provides a nonlinear active in-the-ear hearing protector which can be conveniently acquired off-the-shelf without specialised fitting by trained technicians.

The hearing protector described with reference to the drawing provides a nonlinear active in-the-car hearing protector with a detachable car piece which is easy to manufacture and is inexpensive to the user; the detachable car piece can be easily cleaned by detaching it from the hearing protector, and can be readily replaced if it becomes soiled or dirty to maintain a high degree of hygiene, or replaced if its sound transmission path is irreparably clogged by car wax.

The hearing protector described with reference to the drawings provides a nonlinear active in-the-ear hearing protector with a casing which containing electronic and electroacoustic components, and is transferable from user to user.

Although hearing protector 11 has been described as a single unit for use in protecting the hearing of one ear of a wearer, it should be apparent that two hearing protectors should normally fly be worn by the wearer, one in each ear, to protect both ears from damage caused by exposure to loud sounds.

While there are shown and described present preferred embodiments of the invention it shall be clearly understood that such description is for illustrative purposes only and is not to be construed in a limiting sense since many modifications and alterations may be made without departing from the spirit and scope of the invention which includes every novel feature and combination of features herein disclosed.

The claims defining the invention are as follows:

1. An active in-the-ear hearing protector made suitable to be sealingly inserted, one in each ear canal of a wearer, for protecting the wearer from loud sounds while enabling the wearer to hear sounds at non-harmful sound pressure levels, comprising:
   (a) a casing having distal and proximal ends and an exterior surface between said distal and proximal ends and having in its interior:
      (i) microphone means for converting exterior sounds originating exteriorly of the outer eat to an electrical microphone signal,
      (ii) electronic means for converting said electrical microphone signal to an electrical output signal, said electronic means including electronic compression means for controlling the amplitude of said electrical output signal m be proportional to the amplitude of said electrical microphone signal when the amplitude of said electrical microphone signal is below a pre-determined threshold value, and for automatically limiting the amplitude of said electrical output signal to within a pre-determined narrow dynamic range when the amplitude of said electrical microphone signal increases beyond said pre-determined threshold value so that the amplitude of said electrical output signal is not allowed to exceed a pre-determined maximum amplitude,
      (iii) sound reproducer means for producing sound waves in response to said electrical output signal,
      (iv) sound transmitting means sealingly attached to the acoustic outlet of said sound reproducer means and to the wall of said distal end of said casing for delivering sound waves produced by said sound reproducer means to the exterior of said distal end of said casing, whereby Transmission of said exterior sounds through said casing and then said sound transmitting means is minimized,
      (v) battery means for supplying power for operation of said active hearing protector,
   (b) an on/off switching means which is partly located exteriorly to and proximally of said easing, whereby the electrical power supplied by said battery can be switched on or off exteriorly to said casing at the proximal end of said casing,
   (c) a user detachable ear piece comprising:
      (i) a sound transmitting tube,
      (ii) a polymeric retarded recovery foam member having distal and proximal ends, said foam member sealingly surrounding said sound transmitting tube, whereby an acoustic seal is formed between said sound transmitting tube and said foam member especially when said foam member is mechanically compressed to miniraise transmission of said exterior sounds to the eardrum, said foam member defining a substantially cylindrical element having a slow compression recovery rate, whereby said ear piece may be mechanically compressed and inserted distal end first into an ear canal of the wearer and will thereupon expand to form an elongated acoustic seal therein between the ear piece and a substantial surface area of the ear canal to minimise transmission of said exterior sounds to the eardrum,
      (iii) connector means attached to said proximal end of said polymeric foam member for detachably and scalingly attaching said detachable ear piece to the distal portion of said casing and for sealingly connecting said sound transmitting means attached to said sound reproducer means to said sound transmitting tube in said detachable ear piece, whereby sounds produced by said sound reproducer means are transmitted through an acoustically sealed sound transmission path comprising said sound transmitting means in said casing and said sound transmitting tube in said ear piece to the ear canal and eardrum so that the transmission of said exterior sounds through said connector means to the eardrum is minimised.

2. An active in-the-ear hearing protector as claimed in claim 1, wherein said sound transmitting tube in said foam member is a flexible tube with a diameter substantially smaller than the diameter of the ear canal, whereby case of insertion of said ear piece into ear canal can be achieved.

3. An active in-the-ear hearing protector as claimed in claim 1, wherein said sound transmitting tube extends for a short distance beyond said distal end of said foam member into the ear canal, whereby said sound transmitting tube is not blocked by the foam material at said distal end of said foam member to ensure that sounds produced by said sound reproducing means can reach the ear canal without any inadvertent obstruction.

4. An active in-the-ear heating protector as claimed in claim 1 wherein said sound transmitting tube has an outwardly flared end at said distal of said foam member, whereby said sound transmitting tube is not blocked by the foam material at said distal end of said foam member to ensure that sounds produced by said sound reproducing means can reach the ear canal without any inadvertent obstruction.

5. An active in-the-ear hearing protector as claimed in claim 1, wherein said casing is made of plastic.

6. An active in-the-ear hearing protector as claimed in claim 1, wherein said distal portion of said casing is cylindrical with a flat bottom surface at said distal end.

7. An active in-the-ear hearing protector as claimed claim 1 wherein said sound transmitting means in said casing is a flexible plastic tube sealingly inserted into a centre hole in said bottom surface but does not extend beyond said distal end of said casing.

8. An active in-the-ear hearing protector as claimed in claim 1 wherein said exterior surface of said distal portion of said casing is formed with a male screw thread.

9. An active in-the-ear hearing protector as claimed of claim 1, wherein said connector means comprises a hollow cylindrical connector which is closed at the distal end of said connector means by a flat end surface, a centre hole in said end surface concentric with said centre hole in said bottom surface at said distal end of said casing, and a resilient washer with a centre hole concentric with said centre hole in said end surface.

10. An active in-the-ear hearing protector as claimed in claim 9, wherein said hollow cylindrical connector is made of plastic.

11. An active in-the-ear hearing protector as claimed in claim 9, wherein said resilient washer is contiguous with said end surface.

12. An active in-the-ear hearing protector as claimed in claim 9 wherein the interior surface of said hollow cylindrical connector is formed with a female screw thread for mating with said male screw thread on said distal portion of said casing.

13. An active in-the-ear hearing protector as claimed in claim 9 wherein said sound transmitting tube in said detachable eat piece is inserted through said centre hole in said end surface of said hollow cylindrical connector but does not extend beyond said end surface, whereby when said detachable ear piece is attached to said casing by mating of said male and female screw threads an acoustically sealed sound transmission path is formed from said sound reproducing means to the ear canal and eardrum by mechanically compressing the resilient washer between said end surface of said hollow cylindrical connector and said bottom surface of said casing.

14. An active in-the-car hearing protector as claimed in claims 9 wherein said resilient washer is made of rubber.

15. An active in-the-car hearing protector as claimed in claim 9 wherein said resilient washer is made of cork.

16. An active in-the-car hearing protector as claimed in claim 9 wherein said resilient washer is made of felt.

17. An active in-the-car hearing protector as claimed in claim 1 wherein said connector means comprises a hollow cylindrical connector which is closed at the distal end of said connector means by a flat end surface, and a centre hole in said end surface concentric with said centre hole in said bottom surface at said distal end of said casing.

18. An active in-the-car hearing protector as claimed in claim 17, wherein said hollow cylindrical connector is made of plastic.

19. An active in-the-car hearing protector as claimed in claim 17 wherein the interior surface of said hollow cylindrical connector is form female screw thread for mating with said male screw thread on said distal portion of said casing.

20. An active in-the-ear hearing protector as claimed in claim 17 wherein said sound transmitting robe in said detachable ear piece is inserted through said centre hole in said end surface of said hollow cylindrical connector but does not extend beyond said end surface, whereby when said detachable ear piece is attached to said casing by mating of said male and female screw threads an acoustically sealed sound mission path is formed from said sound reproducing means to the ear canal and eardrum by contiguously attaching said end surface of said hollow cylindrical connector to said bottom surface of said casing.

21. A hearing protector comprising a sound processor for receiving at an input thereof exterior sound and generating therefrom at an output thereof corresponding processed sound limited to intensity not exceeding a predetermined sound pressure level, and an earpiece detachably mounted to said sound processor and having sound channeling means in the form of a tube for passage of said processed sound away from said sound processor, said hearing protector being insertable into an ear canal so as to position said sound processor for receiving at said input said exterior sound, being sound originating exteriorially of said ear canal, and for directing said processed sound, as generated from said exterior sound by said sound processor, to an eardrum via said sound channeling means of said earpiece, said earpiece having first acoustic sealing means formed of a retarded recovery resilient material which is compressible to enable the earpiece to be inserted into the ear canal, but which then recovers to form a tight first acoustic seal between the earpiece and the ear canal, such as to preclude sound from passing from the outer ear through the earpiece to the eardrum via the ear canal otherwise than through the sound channeling means, second acoustic sealing means being provided effective to provide a second acoustic seal between the output of said sound processor and an adjacent input end of the sound channeling means, to preclude sound other than said processed sound from entering the sound channeling means, said retarded recovery resilient material sealingly surrounding said tube to form a third acoustic seal between the ear plug member and the exterior of the sound channeling means, said acoustic seals being effective to preclude direct transmission of said exterior sound to the eardrum.

22. A hearing protector as claimed in claim 21 having a casing which incorporates said sound processor and which is attached to said earpiece by a connector means, said casing having an acoustic inlet positioned to receive said exterior sound when said casing is attached to said earpiece and when said hearing protector is inserted into the outer ear.

23. A hearing protector as claimed in claim 22 wherein said connector means holds said second acoustic sealing means between the casing and the earpiece so as to provide said second acoustic seal.

24. A hearing protector as claimed in claim 23 wherein said second acoustic sealing member comprises a resilient washer which is axially compressed by said connector means.

25. A hearing protector as claimed in claim 21 wherein said sound processor comprises a microphone to receive said exterior sound, an electronic circuit and a loudspeaker, said electronic circuit being coupled to receive microphone electrical signal generated by said microphone pursuant to incidence of said exterior sound thereon and to pass an output electrical signal to said loudspeaker for generation of said processed sound for passage into said sound channeling means, said electronic circuit being arranged to limit said output electrical signal as passed therefrom to said loudspeaker such as not to exceed a value which causes intensity of said processed sound to exceed said predetermined sound pressure level.

26. A hearing protector comprising a sound processor for receiving at an input thereof exterior sound and generating therefrom at an output thereof corresponding processed sound limited to intensities not exceeding a predetermined sound pressure level, and an ear piece detachably mounted to said sound processor and having sound channeling means for passage of said processed sound away from said sound processor, said hearing protector being insertable into the ear canal so as to position said sound processor for receiving at said input said exterior sound, being sound originating exteriorly of the outer ear, and for directing said processed sound, as generated from said exterior sound by said sound processor, to the ear drum via said sound channeling means of said ear piece, said ear piece having first acoustic sealing means formed of a retarded recovery resilient material which is compressible to enable the ear piece to be inserted into the ear canal, but which then recovers to form a tight first acoustic seal between the ear piece and the ear canal, such as to preclude sound from passing from the outer ear through the ear piece to the ear drum via the ear canal otherwise than through the sound channeling means, second acoustic sealing means being provided effective to provide a second acoustic seal between the output of said sound processor and an adjacent input end of the sound channeling means, to preclude sound other than said processed sound from entering the sound channeling means, said acoustic seals being effective to preclude direct transmission of said exterior sound to the ear drum, said sound processor being incorporated into a casing which is attached to said ear piece by a connector means, said casing having an acoustic inlet positioned to receive said exterior sound when said casing is attached to said ear piece and when said hearing protector is inserted into the outer ear, said connector means holding said second acoustic sealing means between the casing and the ear piece so as to provide said second acoustic seal.

27. A hearing protector comprising a sound processor for receiving at an input thereof exterior sound and generating therefrom at an output thereof corresponding processed sound limited to intensities not exceeding a predetermined sound pressure level, and an ear piece detachably mounted to said sound processor and having sound channeling means for passage of said processed sound away from said sound processor, said hearing protector being insertable into the ear canal so as to position said sound processor for receiving at said input said exterior sound, being sound originating exteriorly of the outer ear, and for directing said processed sound, as generated from said exterior sound by said sound processor, to the ear drum via said sound channeling means of said ear piece, said ear piece having first acoustic sealing means formed of a retarded recovery resilient material which is compressible to enable the ear piece to be inserted into the ear canal, but which then recovers to form a tight first acoustic seal between the ear piece and the ear canal, such as to preclude sound from passing from the outer ear through the ear piece to the ear drum via the ear canal otherwise than through the sound channeling means, second acoustic sealing means being provided effective to provide a second acoustic seal between the output of said sound processor and an adjacent input end of the sound channeling means, to preclude sound other than said processed sound from entering the sound channeling means, said acoustic seals being effective to preclude direct transmission of said exterior sound to the ear drum, said sound processor being incorporated into a casing which is attached to said ear piece by a connector means, said casing having an acoustic inlet positioned to receive said exterior sound when said casing is attached to said ear piece and when said hearing protector is inserted into the outer ear, said connector means holding holds said second acoustic sealing means between the casing and the ear piece so as to provide said second acoustic seal; wherein said sound processor comprises a microphone to receive said exterior sound, an electronic circuit and a loudspeaker, said electronic circuit being coupled to receive microphone electrical signal generated by said microphone pursuant to incidence of said exterior sound thereon and to pass an output electrical signal to said loudspeaker for generation of said processed sound for passage into said sound channeling means, said electronic circuit being arranged to limit said output electrical signal as passed therefrom to said loudspeaker such as not to exceed a value which causes intensity of said processed sound to exceed said predetermined sound pressure level.

28. A hearing protector comprising a sound processor for receiving at an input thereof exterior sound and generating therefrom at an output thereof corresponding processed sound limited to intensities not exceeding a predetermined sound pressure level, and an ear piece detachably mounted to said sound processor and having sound channeling means for passage of said processed sound away from said sound processor, said hearing protector being insertable into the ear canal so as to position said sound processor for receiving at said input said exterior sound, being sound originating exteriorly of the outer ear, and for directing said processed sound, as generated from said exterior sound by said sound processor, to the ear drum via said sound channeling means of said ear piece, said ear piece having first acoustic sealing means formed of a retarded recovery resilient material which is compressible to enable the ear piece to be inserted into the ear canal, but which then recovers to form a tight first acoustic seal between the ear piece and the ear canal, such as to preclude sound from passing from the outer ear through the ear piece to the ear drum via the ear canal otherwise than through the sound channeling means, second acoustic sealing means being provided effective to provide a second acoustic seal between the output of said sound processor and an adjacent input end of the sound channeling means, to preclude sound other than said processed sound from entering the sound channeling means, said sound processor being incorporated into a casing which is attached to said ear piece by a connector means, said casing having an acoustic inlet positioned to receive said exterior sound when said casing is attached to said ear piece and when said hearing protector is inserted into the outer ear, said connector means holding holds said second acoustic sealing means between the casing and the ear piece so as to provide said second acoustic seal; said ear piece comprising an inner tube defining said sound channeling means and an earplug member, said earplug member sealingly surrounding said inner tube to form a third acoustic seal between the earplug member and the exterior of the sound channeling means, said acoustic seals being effective to preclude direct transmission of said exterior sound to the ear drum.

29. A hearing protector comprising a sound processor for receiving at an input thereof exterior sound and generating therefrom at an output thereof corresponding processed sound limited to intensities not exceeding a predetermined sound pressure level, and an ear piece detachably mounted to said sound processor and having sound channeling means for passage of said processed sound away from said sound processor, said hearing protector being insertable into the ear canal so as to position said sound processor for receiving at said input said exterior sound, being sound originating exteriorly of the outer ear, and for directing said processed sound, as generated from said exterior sound by said sound processor, to the ear drum via said sound channeling means of said ear piece, said ear piece having first acoustic sealing means formed of an ear plug member formed of retarded recovery resilient material which is compressible to enable the ear piece to be inserted into the ear canal, but which then recovers to form a tight first acoustic seal between the ear piece and the ear canal, such as to preclude sound from passing from the outer ear through the ear piece to the ear drum via the ear canal otherwise than through the sound channeling means, second acoustic sealing means being provided effective to provide a second acoustic seal between the output of said sound processor and an adjacent input end of the sound channeling means, to preclude sound other than said processed sound from entering the sound channeling means, said sound processor being incorporated into a casing which is attached to said ear piece by a connector means, said casing having an acoustic inlet positioned to receive said exterior sound when said casing is attached to said ear piece and when said hearing protector is inserted into the outer ear, said connector means holding holds said second acoustic sealing means between the casing and the ear piece so as to provide said second acoustic seal; said ear piece comprising an inner tube defining said sound channeling means and an earplug member formed by said first acoustic means, said earplug member sealingly surrounding said inner tube to form a third acoustic seal between the earplug member and the exterior of the sound channeling means, said acoustic seals being effective to preclude direct transmission of said exterior sound to the ear drum; said sound processor comprising a microphone to receive said exterior sound, an electronic circuit and a loudspeaker, said electronic circuit being coupled to receive microphone electrical signal generated by said microphone pursuant to incidence of said exterior sound thereon and to pass an output electrical signal to said loudspeaker for generation of said processed sound for passage into said sound channeling means, said electronic circuit being arranged to limit said output electrical signal as passed therefrom to said loudspeaker such as not to exceed a value which causes intensity of said processed sound to exceed said predetermined sound pressure level.

* * * * *